United States Patent [19]
Guenther et al.

[11] Patent Number: 4,802,198
[45] Date of Patent: Jan. 31, 1989

[54] X-RAY EQUIPMENT SUPPORT APPARATUS

[75] Inventors: Werner Guenther; Heinrich Schmitt, both of Bensheim, Fed. Rep. of Germany

[73] Assignee: Siemens Aktiengesellschaft, Berlin and Munich, Fed. Rep. of Germany

[21] Appl. No.: 843,258

[22] Filed: Mar. 24, 1986

[30] Foreign Application Priority Data

Apr. 1, 1985 [DE] Fed. Rep. of Germany ....... 3511907

[51] Int. Cl.⁴ .............................................. H05G 1/02
[52] U.S. Cl. .................................... 378/197; 378/167; 378/193; 248/123.1
[58] Field of Search ............... 378/197, 198, 193, 187, 378/167; 248/123.1, 125, 669

[56] References Cited

U.S. PATENT DOCUMENTS

| | | |
|---|---|---|
| 2,132,076 | 10/1938 | Kotraschek et al. ............... 378/197 |
| 3,467,352 | 9/1969 | Bohler ............................... 248/125 |
| 3,496,354 | 2/1970 | Forsyth .............................. 378/197 |
| 3,575,368 | 4/1971 | Thomas .............................. 248/123 |
| 4,048,509 | 9/1977 | Sieber ............................... 378/197 |

FOREIGN PATENT DOCUMENTS 2282843  3/1976  France .
746599   3/1956  United Kingdom .

OTHER PUBLICATIONS

Mit Uberlegener Technik zu Besseren Ergebnissen Orthopantomograph, Siemens brochure, undated.

Primary Examiner—Carolyn E. Fields
Assistant Examiner—David P. Porta
Attorney, Agent, or Firm—Hill, Van Santen, Steadman & Simpson

[57] ABSTRACT

An apparatus for supporting an X-ray unit in a vertically adjustable manner. The apparatus includes a frame having two posts and a carrier supported between the posts. The post are slotted and the carrier includes guide members received within the slots. The carrier also includes a counterbalance for supporting the carrier between the post. The counterbalance includes a support cable and force element.

27 Claims, 3 Drawing Sheets

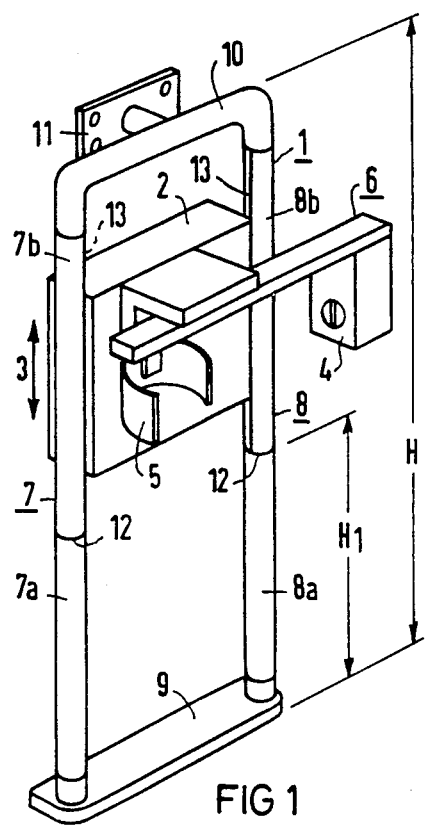
FIG 1
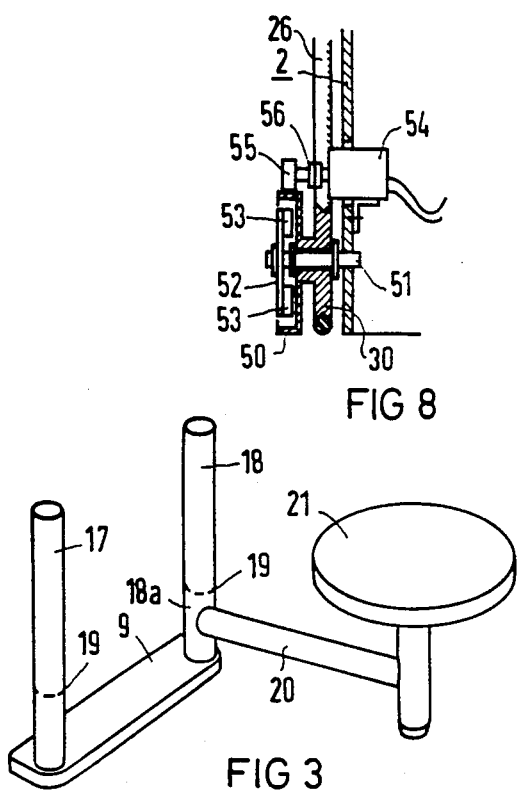
FIG 8
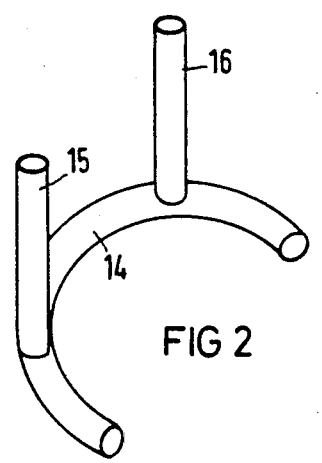
FIG 3
FIG 2
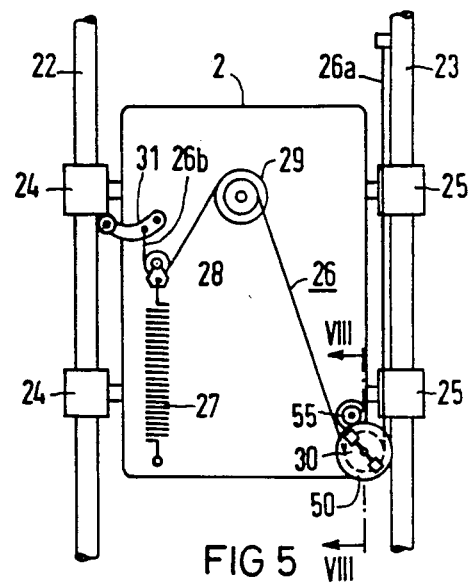
FIG 5

X-RAY EQUIPMENT SUPPORT APPARATUS

BACKGROUND OF THE INVENTION

This invention relates in general to a frame and a carrier, that is vertically adjustable on the frame, for supporting a device or instrument. This invention specifically relates to an apparatus for supporting x-ray equipment in a vertically adjustable manner.

It is known in the medical industry to support an x-ray unit, that includes an x-ray generator and an x-ray film holder, on a carrier that is vertically adjustable with respect to a frame. It is necessary for the x-ray head to be vertically adjustable because of the different heights of patients and the different exposures that are to be taken. It is also necessary, particularly in the field of dental medicine, for the x-ray head to be rotatable with respect to the frame member so that different angles and exposures of the jaw and teeth area of a patient may be taken.

An example of a vertically adjustable x-ray head and frame member is illustrated in Brochure M-D 80/1361 Orthopantomograph 10; WSO8832. As illustrated, an x-ray unit is mounted on a carrier that is vertically adjustable with respect to a support post. The support post supports the carrier member and includes rail members upon which the carrier member is vertically adjustable. The post member has a rectangular cross-section that is hollow and includes counterweights. The counterweights are located on a pulley system and support the weight of the carrier and x-ray unit. Due to the great weight of the x-ray unit, the counterweight force must be at least 90 kilograms. Because of the construction of the cable pulley system and the weight of the x-ray unit, the apparatus provides for little tolerance and an extremely play-free guidance is provided. Moreover, due to the construction of the unit it is an extremely expensive apparatus. Furthermore, the apparatus is very large and takes up a great deal of space. Due to the weight to be supported, it is also difficult to set up the apparatus.

British Pat. No. 746,599 discloses a frame for a carrier unit comprising two spaced post members. The carrier unit is designed to be secured between the post members and is vertically adjustable therebetween. To this end, the carrier includes carriage wheels 5 that are received within guide rails 4 of the post members of the frame. Although this is a simplified construction, due to the construction of the carrier wheels and channel members it is still a relatively expensive construction. Moreover, because the wheels are received in the channel members of the frame, the channel members are relatively wide with respect to the remaining portions of the frame member. The patent fails to disclose any counterbalance member for the carrier unit in the post members.

U.S. Pat. No. 3,575,368 discloses a vertically adjustable counterbalancing x-ray unit suspension support apparatus. The apparatus includes a carrier unit, from which the x-ray unit is suspended, and an elongated frame member. The counterbalancing system is located within the frame member and comprises a compression spring and traction cable guided via a cable cam having a variable diameter, i.e., a fusee. A safety lock member is provided comprising a trapezoidal plate from which the traction cable is suspended. The edges of the trapezoidal plate are constructed so that the plate will be in locking engagement with the guide channel walls of the frame if a cable breaks.

There is a need for an improved frame and x-ray unit carrier that is vertically adjustable with respect to the frame that has an improved and simplified counterbalancing system that overcomes the disadvantages of prior art.

SUMMARY OF THE INVENTION

The present invention provides an apparatus for supporting an x-ray unit in a vertically adjustable manner. The apparatus includes a carrier for supporting an x-ray unit and a frame for supporting the carrier. The frame includes two parallel post members that include longitudinal slots extending a predetermined distance. The carrier includes guide members for being received in the longitudinal slots in a gliding fashion. The carrier also includes a counterbalance member having a force element and a support cable. One end of the support cable is secured to one of the post members and a second end of the cable is secured to the carrier.

In a preferred embodiment of the apparatus, the post members include upper and lower post members. The lower post members being secured to a support strut and the upper post members to a top strut. The upper post members have a hollow cross-sectional construction, define the longitudinal slot, and house a guide rod. The post members can also include a casing. The casing functions, in part, to protect the guide system from dirt and other debris.

In another preferred embodiment, a safety brake is provided. The safety brake prevents the carrier from freefalling if a cable breaks. The carrier includes means for vertically adjusting the carrier either manually or by electrical drive. If the carrier is driven by a motor, an electromagnetic brake can be utilized to stop the carrier at a certain height.

In another preferred embodiment, one of the upper post members includes a pneumatic spring. The pneumatic spring acts as a counterbalance.

The present invention provides an improved apparatus for supporting an x-ray unit that is vertically adjustable. The apparatus has a simple construction but still provides needed stability. Because the counterbalance is contained in the carrier or frame member, the apparatus takes up a relatively minimal amount of space.

Additional advantages and features of the present invention are described in, and will be apparent from, the detailed description of the presently preferred embodiments and the drawings.

BRIEF DESCRIPTION OF THE DRAWINGS

FIG. 1 illustrates a perspective view of the apparatus of the present invention.

FIG. 2 illustrates a perspective view of a further embodiment of the support structure of the apparatus of FIG. 1.

FIG. 3 illustrates a perspective view of another embodiment of the support structure of the apparatus of FIG. 1.

FIG. 5 illustrates a schematic view of the carrier and a portion of the frame of FIG. 1.

FIG. 8 illustrates a cross-sectional view of the apparatus of FIG. 5 taken along lines VIII—VIII of FIG. 5.

DETAILED DESCRIPTION OF THE PRESENTLY PREFERRED EMBODIMENTS

Figure 6:
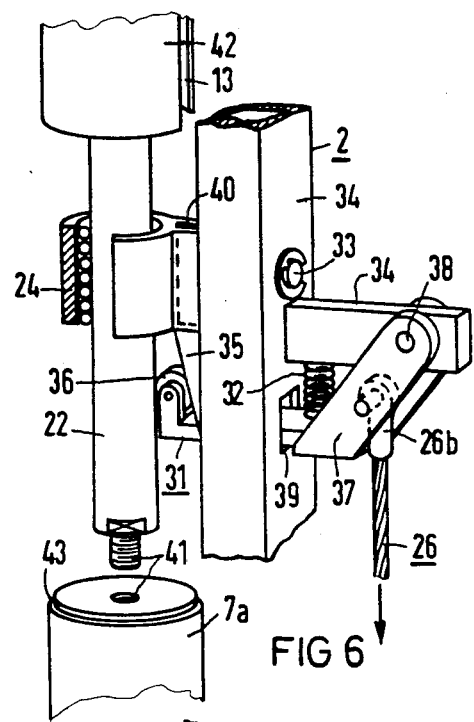
FIG. 6 illustrates a perspective view of the safety lock mechanism of the apparatus of the present invention.

Referring to FIG. 2, the apparatus of the present invention is illustrated. The apparatus includes a frame member 1 that supports a carrier 2. As discussed in more detail below, the carrier 2 and frame 1 are so constructed and arranged that the carrier 1 can be moved in a vertical direction as illustrated by arrow 3.

The carrier 2 supports an x-ray unit 6. The x-ray unit 6 comprises an x-ray generator 4 and an x-ray film holder 5. Preferably, the x-ray unit 6 is rotatably mounted to the carrier 2. This allows the user to take x-rays from a variety of different angles and perspectives with respect to the patient. This is especially important in the dental field. The x-ray unit 6 may be mounted to the carrier 2 as is known in the art. For example, the carrier 2 can have a bracket member that supports the x-ray film holder and pivotally supports the x-ray generator.

The carrier member 2 is supported within the frame 1. The frame 1 includes two parallel post members 7 and 8. The post members 7 and 8 are secured at one end to a top cross-strut 10 and at a second end to a support cross-strut 9. The top and support cross-struts 9 and 10 have a substantially U-shaped construction. The post members 7 and 8 can either be welded to the cross-struts 9 and 10 or secured in some other fashion to the cross-struts. The post members 7 and 8 can be secured to the support strut 9 such that post member 8 is rigidly secured to the support strut and post member 7 is vertically adjustably secured to the support strut 9. Accordingly, if desired, the height of post 7 can be adjusted.

In the preferred embodiment illustrated in FIG. 1, the top cross-strut 10 includes a spacer member 11. The spacer member 11 includes a plate member that may be bolted or secured to a wall by some other means, thereby securing the apparatus to the wall.

In the preferred embodiment illustrated in FIG. 2, a further embodiment of the support cross-strut 9 is illustrated. The support cross-strut includes a C-shaped support member 14 and two post members 15 and 16. The post members 7 and 8 are designed to be welded or secured by some other means to the post members 15 and 16 of the C-shaped support strut 14 illustrated in FIG. 2. Due to the C-shaped support member 14, the support strut provides sufficient support to allow the apparatus to be self-supporting and free standing, i.e., the apparatus does not have to be bolted to a wall.

Referring to FIG. 3, a further embodiment of the support strut 9 is illustrated. As illustrated, the support strut 9 is secured to post members 17 and 18 at a transversely divided location 19. Secured to the support strut post member 18A is an extension arm 20 which is secured a patient chair 21. Because the post member 18a is rotatably mounted to the support strut 9, the patient chair 21 can rotate with respect to the post member 18.

Each post member 7 and 8 includes an upper post member 7b and 8b and a lower post member 7a and 8a respectively. Preferably, the lower post members 7a and 8a have a solid or hollow circular cross-sectional construction. Preferably, the lower post member 7a has a top portion that has a solid cross-sectional construction to support the upper posts 7b and 8b. The top post members 7b and 8b, on the other hand, preferably have a hollow circular cross-sectional construction and include longitudinal slots 13. As will be discussed in more detail below, the longitudinal slots 13 act as a guide means for the carrier 2.

As previously stated, the carrier 2 can be vertically adjusted with respect to the frame 1. Due to the construction of the longitudinal slots 13 in the upper post members 7b and 8b, the lowest possible height the carrier 2 can be lowered to corresponds to the location 12 at which the upper and lower posts 7b and 7a and 8b and 8a are connected (this corresponds to height H1). Preferably this height (H1) will be the lowest height adjustment that will be needed for the x-ray unit 6. It has been found that this height should preferably be approximately 1 meter–1.5 meters. Preferably the overall height (H) of the apparatus should be approximately 2.4 meters.

Because of the tubular structure of the post members 7 and 8, the apparatus of the present invention is easily adaptable and modifiable. Accordingly, the apparatus can be modified based on the end user's needs. For example, the height of the apparatus and design of the base strut 9 are easily adaptable. Indeed auxiliary equipment, such as a patient chair, can be easily added to the apparatus. Moreover, because the post members 7 and 8 comprise post members 7a and 7b and 8a and 8b, rather than a single post structure, considerably smaller packaging units are provided in comparison to prior art units. Accordingly, the apparatus is easier to transport and set up than some prior art apparatus.

Although the post members 7 and 8 are illustrated as being of a tubular construction, it is possible that the post members 7 and 8 can have another shape other than a circular cross-sectional shape.

Figure 4:
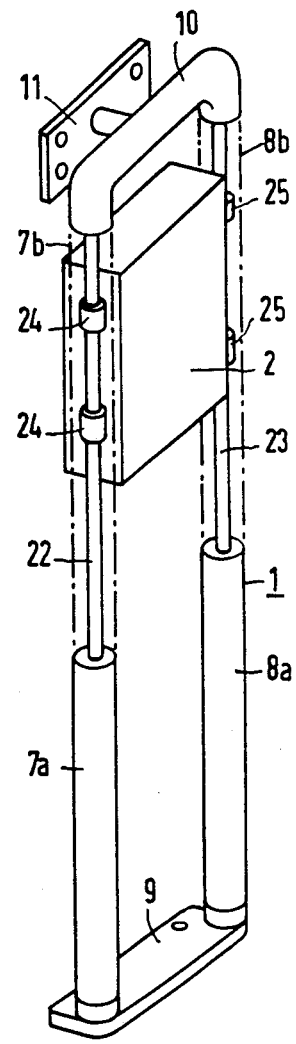
FIG. 4 illustrates the carrier and frame of the apparatus of FIG. 1 with parts of the frame illustrated in phantom lines.

Referring to FIG. 4, the frame 1 and carrier 2 are illustrated. For purposes of illustration, the upper post members 7b and 8b are illustrated in phantom lines in FIG. 4. As illustrated, located within the upper post members 7b and 8b are guide rods 22 and 23 respectively. Received on the guide rods 22 and 23 are guide members 24 and 25. The guide members 24 and 25 are secured to the carrier member 2. To this end, guide members 25 are rigidly secured to carrier member 2 and, as discussed in detail below, guide members 24 are loosely secured to the carrier member 2.

The guide rods 22 and 23 are secured to the ends of the upper cross-strut 10 and to the lower post member 7a and 8a. The guide rods 22 and 23 can be secured to the cross-strut 10 and to the lower post members 7a and 8a by any means known in the art and in the embodiment illustrated are secured by a screw type construction. To this end, as illustrated in FIG. 6, the guide rods 22 and 23 include a threaded portion that is received within a threaded aperture in the lower post members 7a and 8a and the post member of the upper cross-strut 10.

In order to support the carrier 2 in a vertically adjustable manner within the frame 1, a counterbalancing apparatus is provided. FIG. 5 illustrates the counterbalancing apparatus of the present invention. The counterbalancing apparatus includes a support cable 26 which is secured at one end 26b to the carriage 2 and at a second end 26a to the guide rod 23. the support cable 26 is received around a pulley 29 and a deflection roller 28. The deflection roller 28 is secured to a bracket and loaded by a tension spring 27. The suspension cable 26 is further received by a second deflection roller 30 secured to a bottom portion of the carrier 2.

The counterbalance apparatus is constructed so that upon vertical movement of the carrier 2 the force exerted by the tension spring on the deflection roller 28 is increased or decreased accordingly. The changing force of the spring member 27 causes the roller 28 to be pulled downwardly or move upwardly. By varying the force exerted on the roller 28, the weight, and thereby vertical position, of the carrier unit 2 and x-ray unit 6 is compensated for.

As previously stated, the carrier 2 is vertically moveable between the frame 1 on the guide rods 22 and 23. Referring to FIG. 6, a portion of the carrier 2 and frame 1 is illustrated. The guide members 24 and 25 are constructed so that they move vertically on the guide rods 22 and 23 easily. To this end, as illustrated, the guide members 24 and 25 can include ball bearing bushings disposed against the guide rods 22 and 23.

As previously stated, the guide member 24 is loosely secured to the carrier member 2. To this end, guide member 24 is secured to the carrier member 2 by a pin 33. The pin 33 is rigidly connected to the frame 34 of the carrier 2. However, the pin 22 allows guide member 24 to move slightly in an axial direction towards the pin 33 and the frame 34 of the carrier 2. This prevents the carrier 2 from tilting within the frame member 1.

FIG. 6 also illustrates the safety brake apparatus of the present invention. Due to the construction of the guide member 24 and portions of the frame member 34 of the carrier 2, a safety brake system is provided that prevents the free-fall of the carrier 2 if the supporting cable 26 breaks. To this end, the guide member 24 includes a wedge portion 35 having a inclined surface. Located on the wedge 35 and specifically on the inclined surface is a roller member 36. The roller member 36 is secured at one end to a rocker arm 37. The rocker arm 37 is tiltably secured to the frame 34 at another end by a pin 38.

The support cable 26 is secured to the carrier 2 by being secured to the rocker arm 37. To this end, an end 26b of the support cable 26 is secured to the rocker arm 37. When the support cable 26 is supporting the carrier 2, the support cable 26 exerts a force downwardly (in the direction of the arrow) causing the rocker arm 37 to be urged against a detent 39 in the frame 34. In this position, the rocker arm 37 biases the roller member 36 away from the guide rod 22.

The rocker arm 37 is also secured to a tension spring 32. The tension spring 32 urges the rocker arm 37 upwardly. Accordingly, if the support cable 26 does not urge the rocker arm 37 downwardly, the tension spring 32 will the cause the rocker arm, and therefore the roller member 37, to move upwardly. This will cause the roller member 37 to ride the inclined surface of the slant of the wedge member 35 causing the roller member 36 to wedge itself between wedge member 35 and the guide rod 22 arresting any movement of the carrier 2 with respect to the guide rods 22 and 23. Accordingly, if the cable 26 does not support the carrier, i.e., if the support cable breaks, the roller member 36 in cooperation with the guide rod 22 will prevent the carrier 2 from moving downwardly. This therefore provides a safety brake for the apparatus of the present invention.

As illustrated in FIG. 5, the support cable 26 is designed to be received within a portion of the guide member 25. To this end, the guide members 25 include a slotted member 40 as illustrated in FIG. 6. Of course, the guide members 25 can include another form or means for receiving the support cable 26 rather than a slot, e.g., a recess, passage or hole.

The upper post members 7b and 8b include a casing member 42 with a longitudinal slot 13. As previously discussed, the longitudinal slot 13 is designed to receive and allow a portion of the guide members 24 and 25 to move vertically therein. As illustrated in FIG. 6, the lower post member 7a and 8a include a shoulder member 43. The shoulder member 43 is defined by a recess portion of the top portion of the lower post member 7a and 8a. The shoulder member 43 is designed and constructed so that the casing member 42 is seated on the shoulder member 43 when the upper post members 7b and 8b are secured to the lower post members 7a and 8a.

Figure 7:
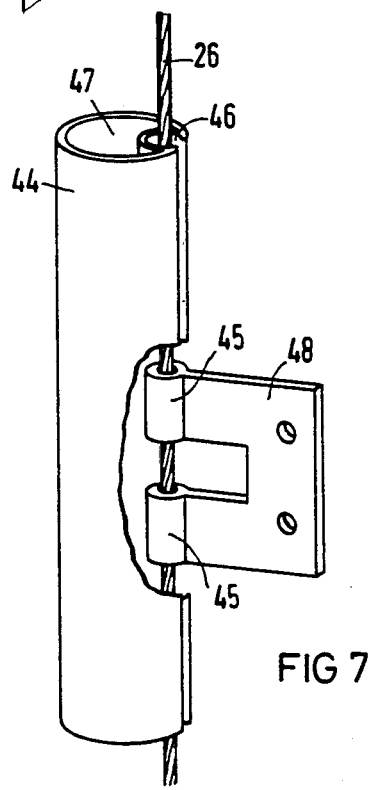
FIG. 7 illustrates a perspective view of a further embodiment of the frame and carrier guide member of the present invention.

The casing member 42 is preferably constructed from a rolled sheet of metal. In the preferred embodiment illustrated in FIG. 7, the casing member 44, comprises a guide track for the carrier 2. To this end, the casing member 44 includes a guide channel 46 and center portion 47. The guide channel 46 is designed to receive the supporting cable 26 and guide member 45 of the carrier 2. The guide channel 46 is constructed so that the guide member 45 can move vertically with respect to the post members and, accordingly, allow the carrier 2 to move vertically. The cross-sectional structure of the casing 44 can be expanded to add additional strength to the guide channel 46. As illustrated, the guide member 45 is secured to a carrier by a plate 48.

Referring to FIGS. 5 and 6 the mechanism for vertically adjusting the carrier 2 is illustrated. As illustrated, the roller 30 is coupled to a pot-shaped drum 50. The pot-shaped drum 50 and roller 30 are rotatably mounted on a shaft 51 that is secured to the carrier 2.

To drive the drum 50, and thereby the roller 30, a friction wheel 55 is mounted against the drum. The friction wheel 55 is coupled to, and driven by, an electrical motor 54. Accordingly, when the electrical motor 54 is actuated, the friction wheel will cause the drum 50, and thereby the roller 30, to rotate. This will cause the roller 30, and thereby the carrier 2, to move up or down the cable 26, therefore, the carrier 2 can be vertically adjusted. A friction clutch 56 is situated between the friction wheel 55 and motor 54 to allow manual vertical adjustment of the carrier 2.

To provide a means for stopping the vertical movement of the carrier 2, a lever 52 is secured to an end of the shaft 51. The lever 52 includes two electromagnetic coils 53. The lever 51 cooperates with the drum 50 to retain the carrier 2 in a desired vertical position. To this end, the drum 50 is constructed from low-retentivity material and the coils 53 form an electromagnetic brake on the drum 50. As is known in the art, the engagement and disengagement of the electromagnetic coils 53 can be accomplished by a switch or other circuit.

Figure 9:
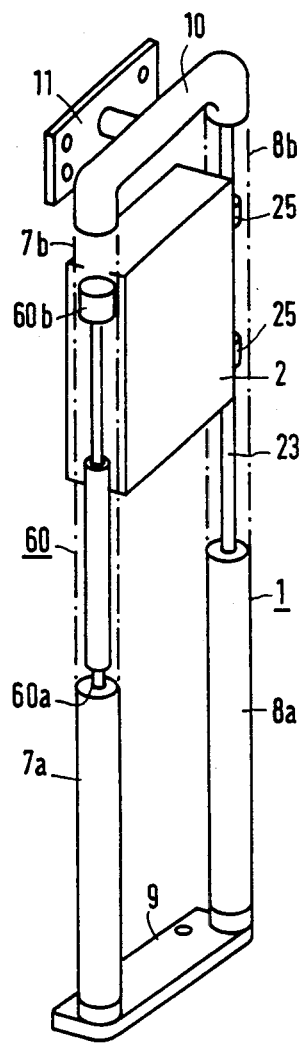
FIG. 9 illustrates a perspective view of a further embodiment of the apparatus of the present invention with parts of the frame illustrated in phantom lines.
Figure 10:
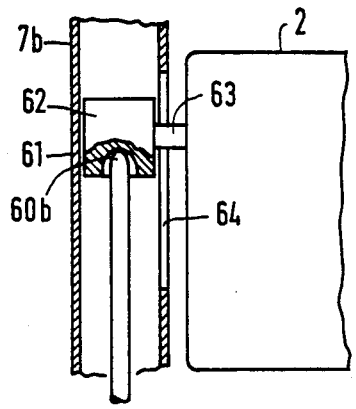
FIG. 10 illustrates a cross-sectional view of a portion of the frame and carrier member of the apparatus of FIG. 9.
Figure 11:
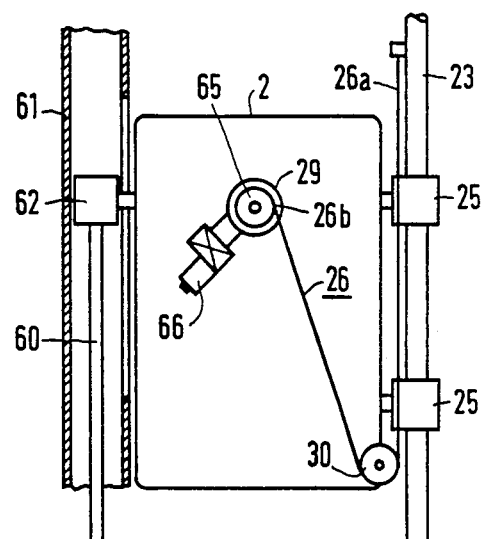
FIG. 11 illustrates a schematic view of the back of the carrier and a portion of the frame of FIG. 9.

A further embodiment of the apparatus of the present invention is illustrated in FIGS. 9 through 11. As illustrated, the apparatus includes an improved counterbalancing apparatus. To this end, the apparatus includes a frame member 1 with post members 7 and 8 that include, as in the previous embodiment, upper post member 7b and 8b and lower post member 7a and 8a. Similarly to the previous embodiment, the upper post member 8b includes a guide rod 23 and the carrier includes guide members 25 that are received on the guide rod 23. Moreover, the guide members 25 are constructed so that they receive a portion of the support cable 26. The support cable 26 is secured at an end 26a to an end of the guide rod 23.

In contrast to the previously described embodiment, the upper post member 7b instead of including a guide rod member includes a pneumatic spring 60. The pneumatic spring 60 is constructed so that one end of the spring 60a is secured to an end of the lower post member 7a, and the second, piston end 62 of the pneumatic spring 60 is secured to the carrier 2 by a rod 63. The piston end 62 is constructed so that it receives an end 60b of the pneumatic spring 60. Accordingly, the piston end 62 acts as a floating guide member within the casing 61 of the upper post member 7b.

The pneumatic spring 60 is housed in a casing 61 of the upper post member 7b. The casing 61 of the upper post member 7b includes a slot member 64 that extends for a sufficient vertical distance that one may wish to adjust the carrier member 2. The slot member 64 has a width that is slightly greater than the width of the pin 63. Accordingly, the carrier member 2 and specifically the pin member 63 can move vertically within the slot member 64.

Pneumatic springs exhibit inherent features that are not desirable for its use as a counterbalance. In order to counteract the variations caused by the pneumatic spring, for example, increased spring force, the pneumatic spring 60 only counterbalances a portion of the weight of the carrier 2 and x-ray unit 6. The remaining portion of the weight is counterbalanced by a second counterbalancing element, or second force element, located on the carrier 2.

The second counterbalancing element located on the carrier 2 comprises an electrically driven cable roller 65. The cable roller 65 includes a DC geared motor 66. One end 26b of the cable 26 is secured to the cable roller 65 which is driven by the DC geared motor 66.

the pneumatic spring 60 is constructed so that it does not support the entire weight of the carrier 2 and x-ray unit 6. Accordingly, the weight of the carrier 2 and the x-ray unit 6 is slightly greater than the maximum counterforce exerted by the pneumatic spring 60. The electrically driven cable roller 65, and specifically the geared motor 66, is designed so that it only exerts the force differential between the dead-weight of the carrier 2 and the x-ray unit 6 and the counterforce of the pneumatic spring 60. Therefore, the combination of the pneumatic spring 60 and motor 66 and roller 65 counterbalances the weight of the carrier 2 and x-ray unit 6.

The embodiment illustrated in FIGS. 9–11 provides for a comparatively simple counterbalance apparatus that allows for the vertical adjustment of the carrier 2. Moreover, due to the construction of the pneumatic spring 60 a safety brake system is not necessary. Of course, the pneumatic spring device 60 does not have to be located within one of the post member 7 or 8 and, for example, can be located outside the post, e.g., the pneumatic spring 60 can be supported against the carrier 2 with the second end supported against the support strut 9.

It should be understood that various changes and modifications to the preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. An apparatus for supporting an x-ray unit in a vertically adjustable manner comprising:
   a carrier, the x-ray unit being securd to the carrier;
   a frame for supporting the carrier and x-ray unit, the frame including two parallel post members, the post members including longitudinal slots extending for a predetermined distance;
   the carrier including guide members for being received in the longitudinal slots of the post members in gliding fashion and the carrier including a counterbalance member having a force element and a support cable, one end of the support cable being secured to one of the post members and a second end of the support cable being secured to the carrier;
   a safety brake for preventing the carrier from free falling within the frame, the safety brake including wedging means supported from the carrier for wedging between a guide rod in the post member and the carrier to prevent downward movement of the carrier, the one end of the support cable being secured to the one post member and the second end being secured to the wedging means, the support cable exerting a force on the wedging means;
   the carrier includes deflection rollers through which the support cable passes, one of the deflection rollers is coupled to means for adjusting the height of the carrier, the means for adjusting the height of the carrier includes a brake wherein the means for adjusting the height of the carrier is an electrically driven motor and the electrically driven motor and brake are connected to a common drum that is coupled to the deflection roller.

2. The apparatus of claim 1 wherein the post members each are divided into an upper and lower post member, the upper and lower post member having a substantially equal length and being secured together.

3. The apparatus of claim 2 including:
   a support strut for supporting the apparatus on a surface, an end of the lower post members being secured to the support strut; and
   a top strut, an end of the upper post members being secured to the top strut.

4. The apparatus of claim 3 wherein:
   the lower post members have an upper end portion member having solid cross-sectional construction; and
   the upper post members have a hollow cross-sectional construction and the longitudinal slot extends for the length of the upper post member.

5. The apparatus of claim 1 wherein the unit is an x-ray unit including an x-ray generator and an x-ray film holder both supported by the carrier.

6. The apparatus of claim 1 wherein:
   the post members each include an upper and lower post member, the upper post members having a hollow cross-sectional construction and including the longitudinal slot, the upper post members housing guide rods; and the guide members of the carrier including means for being received on the guide rods so that the guide members can glide up and down the guide rods.

7. The apparatus of claim 1 wherein the post members each include an upper and lower post member, the upper post member including a jacket casing that defines the longitudinal slots of the post members.

8. The apparatus of claim 7 wherein the jacket casing is constructed from sheet metal.

9. The apparatus of claim 1 wherein one set of guide members are rigidly connected to the carrier and a second set of guide members are loosely connected to the carrier.

10. The apparatus of claim 1 wherein:
the carrier including a inclined surface portion;
the wedging means includes a roller member and is secured to a tension spring; and
the tension spring and support cable cooperating so that the roller member moves up the inclined surface wedging between the carrier and guide rod if the force exerted by the support cable is not sufficiently great.

11. The apparatus of claim 1 wherein
the force element of the counterbalance is a tension spring that exerts a force on the support cable, the force exerted by the tension spring compensates for the weight of the carrier and x-ray unit.

12. The apparatus of claim 1 wherein the force element of the counterbalance member includes a cable roller to which the support cable is coupled, the cable roller being driven by an electrically driven geared motor.

13. The apparatus of claim 1 including a pneumatic spring, one end of the pneumatic spring being secured to the carrier, the other end being secured to one of the post members.

14. The apparatus of claim 1 wherein the post members each include an upper and lower member, and the pneumatic spring is located in the upper member of the post member and supported at one end on the lower post member.

15. The apparatus of claim 14 wherein the upper post member includes a jacket casing that houses the pneumatic spring, the jacket casing defining the longitudinal slot, and one of the guide members of the carrier being supported on an end of the pneumatic spring.

16. An apparatus for supporting an x-ray unit in a vertically adjustable manner comprising:
a carrier, the x-ray unit being secured to the carrier;
a frame for supporting the carrier and x-ray unit in a vertically adjustable manner, the frame including two parallel post members, the post members each including an upper and lower post member, the upper post members having a slot;
the carrier including a guide member that is received in the slot for allowing the carrier to be vertically moveable within the frame; and
the carrier including a counterbalance member for supporting the carrier at a vertical position within the frame, the counterbalance member including a force element and a support cable secured at one end to one of the post members and at a second end to the carrier.

17. The apparatus of claim 16 wherein the upper post members have a hollow cross-sectional construction and at least one of the upper post members includes a guide rod for receiving a guide member of the carrier.

18. The apparatus of claim 17 wherein one of the upper post members includes a pneumatic spring member that is coupled to the carrier for supporting a portion of the weight of the carrier and x-ray unit.

19. The apparatus of claim 17 including a safety brake for preventing the free-fall of the carrier within the frmae, the safety brake including wedging means for preventing movement of the carrier with respect to the guide rod, the wedging means having a wedging member carried on the carrier, the second end of the cable being secured to this wedging member.

20. The apparatus of claim 16 including electrically driven means for vertically adjusting the carrier, the electrically driven means being secured to carrier and driving a roller to which the second end of support cable is coupled.

21. An apparatus for supporting an x-ray unit in a vertically adjustable manner comprising:
a frame including a top strut, a support strut, and two parallel post members, the post members each defining a longitudinal slot;
a carrier for supporting the x-ray unit, the carrier being received between the post members and being vertically adjustable therebetween, the carrier including guide members that are received within the slots of the post members, and means for supporting the carrier in a vertical position between the post members, the means for supporting the carrier member including a support cable secured at one end to the carrier and at a second end to a post member and a force element; and
the carrier includes means for adjusting the vertical position of the carrier in the frame and the carrier includes a safety brake for preventing the free fall of the carrier within the frame.

22. The apparatus of claim 21 wherein one of the post members includes a pneumatic spring member for supporting a portion of the weight of the carrier.

23. The apparatus of claim 21 wherein:
the force element of the means for supporting the carrier member includes a roller that is coupled to an electrically driven motor;
one of the post members includes a pneumatic spring that is coupled to a guide member of the carrier; and
the pneumatic spring and force element cooperate to support the carrier member at a vertical position in the frame.

24. An apparatus for supporting an x-ray unit in a vertically adjustable manner comprising:
a carrier, the x-ray unit being secured to the carrier;
a frame for supporting the carrier and x-ray unit in a vertically adjustable manner, the frame including two parallel post members, the post members each including an upper and lower post member which are selectively disassemblable for purposes of transporting said apparatus, the upper post members being hollow and having a longitudinal slot;
the carrier including a guide member on each lateral side that is received in the slot and extend into the hollow interior of the post member for allowing the carrier to be vertically movable within the frame;
the carrier including a counterbalance member for supporting the carrier at a vertical position within the frame, the counterbalance member including a force element and a support cable secured at one end to one of the post members and at a second end to the carrier; and a safety brake for preventing the free-fall of the carrier within the frame, the safety brake including wedging means for preventing movement of the carrier with respect to the upper post member the wedging means having a wedging member carried on the carrier, the second end of the cable being secured to this wedging member.

25. The apparatus of claim 24 wherein at least one of the upper post members includes a guide rod for receiving a guide member of the carrier.

26. The apparatus of claim 24 wherein one of the upper post members includes a pneumatic spring member that is coupled to the carrier for supporting a portion of the weight of the carrier and x-ray unit.

27. The apparatus of claim 24 including electrically driven means for vertically adjusting the carrier, the electrically driven means being secured to carrier and driving a roller to which the second end of the support cable is coupled.

* * * * *